(12) United States Patent
Oldenburg et al.

(10) Patent No.: US 8,624,070 B2
(45) Date of Patent: Jan. 7, 2014

(54) PHOSPHORUS RECOVERY FROM HYDROTHERMAL TREATMENT OF BIOMASS

(75) Inventors: Paul D. Oldenburg, Easton, PA (US); James R. Bielenberg, Houston, TX (US); Virginia M. Roberts, Summit, NJ (US); Halou Oumar-Mahamat, Belle Mead, NJ (US); Peter J. Domaille, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 111 days.

(21) Appl. No.: 13/285,691

(22) Filed: Oct. 31, 2011

(65) Prior Publication Data
US 2012/0096762 A1    Apr. 26, 2012

Related U.S. Application Data (60) Provisional application No. 61/422,400, filed on Dec. 13, 2010, provisional application No. 61/422,438, filed on Dec. 13, 2010, provisional application No. 61/422,427, filed on Dec. 13, 2010, provisional application No. 61/422,455, filed on Dec. 13, 2010.

(51) Int. Cl.
*C07C 1/00*    (2006.01)

(52) U.S. Cl.
USPC ...... 585/240; 585/242; 435/257.1; 435/257.6

(58) Field of Classification Search
USPC ........ 585/240, 242; 44/605; 435/257.1–257.6
See application file for complete search history.

(56) References Cited

U.S. PATENT DOCUMENTS

| | | | |
|---|---|---|---|
| 4,028,221 A | 6/1977 | Sze et al. | |
| 4,396,786 A | 8/1983 | Bond et al. | |
| 6,053,954 A * | 4/2000 | Anderson et al. | 44/280 |
| 6,180,845 B1 * | 1/2001 | Catallo et al. | 585/240 |
| 7,262,331 B2 * | 8/2007 | van de Beld et al. | 585/240 |
| 7,666,296 B2 | 2/2010 | Roy-Auberger | |
| 7,943,791 B2 | 5/2011 | McNeff | |
| 7,955,508 B2 * | 6/2011 | Allan et al. | 210/749 |
| 8,075,642 B2 | 12/2011 | Dumesic et al. | |

(Continued)

FOREIGN PATENT DOCUMENTS

| | | |
|---|---|---|
| CN | 101591573 | 12/2009 |
| DE | WO9915605 | 4/1999 |

(Continued)

OTHER PUBLICATIONS

Shigeki Sawayama, et al., "CO2 fixation and oil production through microalga," Energy Conversion and Management (1995), vol. 36, Nos. 6-9, pp. 729-731.

(Continued)

*Primary Examiner* — Nina Bhat
(74) *Attorney, Agent, or Firm* — David M. Weisberg (57) ABSTRACT

Biomass based feeds are processed under hydrothermal treatment conditions to produce a hydrocarbon liquid product and a solids portion. The solids portion can contain a portion of the phosphorus from the biomass feed. The amount of phosphorus in the solids portion can be increased for some biomass feeds by adding a multivalent metal to the feed. The phosphorus from the solids portion can be recycled for further use, such as for growth of additional biomass.

29 Claims, 2 Drawing Sheets

(56) References Cited

U.S. PATENT DOCUMENTS

| | | | |
|---|---|---|---|
| 8,487,148 B2* | 7/2013 | Roberts et al. | 585/240 |
| 2008/0050792 A1 | 2/2008 | Zmierczak et al. | |
| 2008/0058563 A1 | 3/2008 | Dumesic | |
| 2008/0160593 A1 | 7/2008 | Oyler | |
| 2008/0188676 A1* | 8/2008 | Anderson et al. | 554/21 |
| 2009/0084026 A1 | 4/2009 | Miller | |
| 2009/0090046 A1* | 4/2009 | O'Connor et al. | 44/307 |
| 2009/0158638 A1 | 6/2009 | Hatcher et al. | |
| 2009/0308787 A1 | 12/2009 | O'Connor et al. | |
| 2010/0050502 A1 | 3/2010 | Wu et al. | |
| 2010/0076238 A1 | 3/2010 | Brandvold et al. | |
| 2010/0137665 A1 | 6/2010 | Chen | |
| 2010/0154305 A1 | 6/2010 | Elliott et al. | |
| 2010/0170147 A1 | 7/2010 | McNeff et al. | |
| 2010/0176026 A1 | 7/2010 | Cole et al. | |
| 2010/0228067 A1 | 9/2010 | Peterson et al. | |
| 2010/0233761 A1 | 9/2010 | Czartoski et al. | |
| 2011/0245444 A1 | 10/2011 | Miller et al. | |
| 2011/0287503 A1 | 11/2011 | Lupton et al. | |
| 2012/0090223 A1 | 4/2012 | Kokayeff et al. | |

FOREIGN PATENT DOCUMENTS

| | | | |
|---|---|---|---|
| EP | 429995 | | 2/1996 |
| GB | 2166154 | | 4/1986 |
| JP | 5244908 | | 9/1993 |
| JP | 2009191008 | | 8/2009 |
| JP | 2009242202 | A | 10/2009 |
| US | WO9630464 | | 10/1996 |
| WO | WO2010/021753 | * | 2/2010 |
| WO | WO2010030196 | A1 | 3/2010 |
| WO | WO2010030197 | A | 3/2010 |
| WO | WO2010134077 | A2 | 11/2010 |
| WO | WO2011126382 | A1 | 10/2011 |

OTHER PUBLICATIONS

"Recent progress in converting biomass to biofuels and renewable chemicals in sub- or supercritical water," Biofuels (2010), vol. 1, No. 1, pp. 109-128.

Zou Shuping, "Thermochemical catalytic liquefaction of microalgae and properties of bio-oil," Taiyangneng Xuebao/Acta Energiae Solaris Sinica (Nov. 2009), vol. 30, No. 11, pp. 1571-1576. English Abstract Only.

Biomass resource facilities and biomass conversion processing for fuels and chemicals, Energy Conversion and Management (Jul. 2001) vol. 42, No. 11, pp. 1357-1378.

"Hydrogen production by gasification of glucose and wet biomass in supercritical water," Advances in Hydrogen Energy (1990), 8, vol. 1, pp. 345-355.

Miguel Herrero, et al., "Sub- and supercritical fluid extraction of functional ingredients from different natural sources: Plants, food-by-products, algae and microalgae: A review," Food Chemistry (2006), vol. 98, No. 1, pp. 136-148.

"Towards sustainable production of biofuels from microalgae," International Journal of Molecular Sciences (2008), vol. 9, No. 7, pp. 1185-1195.

S. Inoue, et al., "Analysis of oil derived from liquefaction of *Botryococcus braunii*," Biomass & Bioenergy (1994) vol. 6, No. 4, pp. 269-274.

"Antioxidants in plant foods and microalgae extracted using compressed fluids," EJEAFChe, Electronic Journal of Environmental, Agricultural and Food Chemistry (2008), vol. 7, No. 8, pp. 3301-3309.

Sekiyu Gakkaishi, "Thermochemical liquefaction of biomass wastes and unused biomass," National Institute Resources and Environment, 1998, vol. 41, No. 1, pp. 11-21 Abstract Only.

Y. Dote, et al., "Recovery of liquid fuel from hydro-carbon-rich microalgae by thermochemical liquefaction," Fuel (1994), vol. 73, No. 12, pp. 1855-1857.

T. Minowa, et al., "Oil production from algal cells of *Dunaliella tertiolecta* by direct thermochemical liquefaction," Fuel (1995), vol. 74, No. 12, pp. 1735-1738.

S. Sawayama, et al., "Possibility of renewable energy production and CO2 mitigation by thermochemical liquefaction of microalgae," Biomass and Bioenergy (1999), vol. 17, No. 1, pp. 33-39.

"Comments on "Thermochemical catalytic liquefaction of the marine microalgae *Duanaliella tertiolecta* and characterization of bio-oils" by Zou et al.," Energy & Fuels (2009), vol. 23, No. 12, pp. 6275-6276.

Elliot "Catalytic hydrothermal gasification of biomass." Sustainable Chemistry and Green Chemistry (online), Apr. 14, 2008 [Retrieved on Mar. 20, 2012], vol. 2, Iss. 3, pp. 254-265, Retrieved from the Internet; <URL: http://onlinelibrary.wiley.com/doi/10.1002/bbb.74/abstract>, see the entire document, especially Figures 1, 2; Tables 1-5.

Y.F. Yang, e t al. "Analysis of energy conversion characteristics in liquefaction of algae," Resources, Conservation and Recycling (Dec. 2004), vol. 43, No. 1, pp. 21-33.

Zou Shuping, "Thermochemical catalytic liquefaction of microalgae and properties of bio-oil," Taiyangneng Xuebao/Acta Energiae Solaris Sinica (Nov. 2009), vol. 30, No. 11, pp. 1571-1576 Abstract Only.

Tylisha M. Brown, et al., "Hydrothermal Liquefaction and Gasification of *Nannochloropsis* sp.," Energy & Fuels (2010), vol. 24, pp. 3639-3646.

Ayhan Demirbas, "Use of algae as biofuel sources," Energy Conversion and Management (2010) vol. 51, No. 12, pp. 2738-2749.

A.B. Ross, et al., "Hydrothermal processing of microalgae using alkali and organic acids," Fuel (2010), vol. 89, No. 9, pp. 234-2243.

Dong Zhou, et al., "Hydrothermal Liquefaction of Macroalgae *Enteromorpha prolifera* to Bio-oil," Energy & Fules (2010) vol. 24, No. 7, pp. 4054-4061.

* cited by examiner

PHOSPHORUS RECOVERY FROM HYDROTHERMAL TREATMENT OF BIOMASS

CROSS-REFERENCE TO RELATED APPLICATIONS

This application relates to and claims priority to U.S. Provisional Patent Application No. 61/422,455 of the same title filed Dec. 13, 2010.

This application is also related to the following co-pending, commonly assigned, applications: (1) U.S. patent application Ser. No. 13/285,519 entitled "Hydrothermal Treatment of Biomass with: Heterogeneous Catalyst" filed Oct. 31, 2011 which claims priority to U.S. Provisional Patent Application No. 61/422,400 of the same title filed Dec. 13, 2010; (2) U.S. patent application Ser. No. 13/285,743 entitled "Catalyst Recovery in Hydrothermal Treatment of Biomass" filed Oct. 31, 2011 which claims priority to U.S. Provisional Patent Application No. 61/422,438 of the same title filed Dec. 13, 2010; and (3) U.S. patent application Ser. No. 13/285,787 entitled "Catalytic Hydrothermal Treatment of: Biomass" filed Oct. 31, 2011 which claims priority to U.S. Provisional Patent Application No. 61/422,427 of the same title filed Dec. 13, 2010.

The contents of each of the above applications are hereby incorporated by reference in their entirety.

FIELD OF THE INVENTION

This invention relates to hydrothermal treatment of various types of biomass, such as algae, to produce hydrocarbon products, such as distillate fuel.

BACKGROUND OF THE INVENTION

Conventional production of fuels and lubricants is still dominated by conversion of mineral petroleum feeds into desired products. In order to supplement and/or replace the conventional sources with renewable forms of energy, a variety of problems must be overcome.

One alternative to conventional fuels and lubricants is to produce comparable fuels and lubricants based on biomass. One advantage of biomass based fuels is that the resulting fuel product may be compatible with existing infrastructure and technologies. Ideally, biomass based fuels and lubricants could be used in a "drop-in" fashion in place of conventional products, allowing the use of a renewable product without having to modify existing equipment.

One option for processing of a biomass type feed is hydrothermal processing. Hydrothermal processing involves exposing a feed to water under elevated temperature and pressure conditions. U.S. Pat. No. 6,180,845 provides an example of this type of process. This patent describes a process for transforming biomass to hydrocarbon mixtures using near-critical or supercritical water. The process can be used on a variety of initial biomass materials. The biomass is processed at pressures from 200 bars (20 MPa) to 500 bars (50 MPa) and at temperatures from 320° C. to 500° C. The atmosphere in the reactor is described as non-oxidizing, and hydrogen is included in an example. About 4 hours is noted as a preferred processing time. The hydrothermal processing is described as producing a "petroleum like liquid", which appears to include a substantial portion of aromatic and polymeric species, as well as some soot and/or carbonized residues. The description mentions that some metals present in the biomass feed, such as Ni or Fe, can alter the types of products generated. The description also mentions that metals can be used to simplify the components of the product mixture, or to remove unwanted compounds. The only metal specifically mentioned as an additive is Cu metal for removal of sulfur compounds such as thiophenes. Nitrogen compounds are identified as another product that can be removed by precipitation with metals, although no examples of a suitable metal are provided. It appears from the description that the additive metals used are "reduced metals", as opposed to metals in an oxidized state.

PCT Publication No. WO 96/30464 provides another example of processing of biomass at supercritical conditions. The application describes processing of wet biomass, such as algae or water hyacinth, to produce gaseous hydrocarbons and hydrogen. The conversion conditions include contacting the biomass with water under supercritical conditions, which is defined as having a temperature of greater than 374° C. and a pressure greater than 22.1 MPa. The conversion takes place in the presence of a carbon based catalyst, such as charcoal or an activated carbon with a high surface area. The process is described as providing rapid and virtually complete gasification of organic matter in a feedstock.

SUMMARY OF THE INVENTION

In one aspect of the invention, a method for hydrothermally processing biomass is provided. The method includes introducing a biomass feed having a phosphorus content and a water to biomass ratio of at least 1:1 into a reaction zone. The biomass feed can be hydrothermally treated under effective hydrothermal treatment conditions to produce a multi-phase product. The multi-phase product can include a solids portion containing at least about 80% of the phosphorus content of the biomass feed. The multi-phase product can be separated to produce at least a gas phase portion, a liquid hydrocarbon product, and the solids portion.

In another aspect of the invention, another method for hydrothermally processing biomass is provided. The method includes adding a multivalent metal to a biomass feed having a phosphorus content. The biomass feed can be contacted with water in the presence of the multivalent metal under effective hydrothermal treatment conditions to produce a multi-phase product. The multi-phase product can include a solids portion containing at least about 80% of the phosphorus content of the biomass feed. The multi-phase product can be separated to produce at least a gas phase portion, a liquid hydrocarbon product, and the solids portion.

In still another aspect of the invention, yet another method for hydrothermally processing biomass is provided. The method includes contacting an algae-containing biomass feed having a phosphorus content with water under effective hydrothermal treatment conditions to produce a multi-phase product. The multi-phase product can include a solids portion containing at least about 80% of the phosphorus content of the algae-containing biomass feed. The multi-phase product can be separated to produce at least a gas phase portion, a liquid hydrocarbon product, and the solids portion. Phosphorus from the solids portion can advantageously be recycled to an algae growth environment.

DETAILED DESCRIPTION OF THE EMBODIMENTS

Overview

One of the difficulties with production of hydrocarbon products from various types of biomass can be handling of products other than carbonaceous. In many instances, the non-carbonaceous products can be viewed as contaminants. Such contaminants can include sulfur-containing compounds and nitrogen-containing compounds formed from sulfur and/or nitrogen present in the biomass.

For some biomass feeds, such as algae feeds or other feeds where cellular material is included in the feed, phosphorus can also represent a noticeable portion of the feed. Unlike sulfur, however, it can be beneficial to view phosphorus as another product to be harvested from processing of a feed. Phosphorus can be incorporated into various cellular structures, such as lipids used for forming cell walls. Because of the importance of phosphorus in developing cellular structures, phosphorus can be a valuable input for growth of biological organisms. The phosphorus required for growth of biological organisms can represent a significant cost in a growth process. Even though phosphorus is not one of the primary saleable products formed from processing of a biomass feed to produce hydrocarbon products, the ability to effectively capture and re-use phosphorus can greatly improve the economics of a hydrocarbon production process.

In various embodiments, methods are provided for hydrothermal treatment of algae feeds (or other biomass based feeds) to produce distillate boiling range products while allowing for improved capture and/or recycling of phosphorus. Hydrothermal treatment of an algae feed can allow for conversion of biomass into molecules having a desired boiling range while also removing at least a portion of impurities that are not desirable in a distillate product, such as nitrogen impurities, oxygen impurities, unsaturated and/or aromatic impurities, metal impurities, and the like. In various embodiments, hydrothermal processing conditions can be adjusted and/or improved to facilitate recovery of phosphorus. This can include increasing the total amount of phosphorus recovered relative to the amount of phosphorus in the feed. This can additionally or alternately include increasing the ratio of phosphorus to carbon in the phosphorus product formed during processing. The methods for improving phosphorus recovery can include introducing multivalent metal, such as multivalent metal cations, into the reaction environment to form metal phosphates. Another option can involve selecting a temperature and/or length of time for hydrothermal processing that improves the amount of phosphorus recovered relative to the feed content and/or the ratio of phosphorus to carbon in the solids formed during reaction.

Algae can contain significant amounts of products such as triglycerides, fatty acids/alcohols, and isoprenoids, which can be converted to valuable products such as transportation fuels and lubricants. However, a number of challenges exist in converting an algae feed into a usable product. One challenge is recovering the desired hydrocarbon molecules from the algae. An option for recovering hydrocarbon products from algae can be to use a solvent extraction based method. Unfortunately, some solvent based methods require use of an algae source that contains little or no water. Dehydration of an algae source to a sufficient degree to allow for this type of solvent extraction can require a high cost of operation. Alternative solvent extraction methods can allow for extraction from an algae sample that contains water. However, a high cost step usually remains, as the solvent has to be separated from the water, for example by distillation.

As an alternative to solvent extraction, hydrothermal processing can be used to extract hydrocarbon products from an algae source. Hydrothermal processing has the advantage that it can be performed without vaporizing water, which can reduce the cost of the process. However, another difficulty with using biomass to produce hydrocarbon products can be the presence of impurities in the biomass. An algae feed can have a relatively high concentration of molecules that can contain, inter alia, sulfur, nitrogen, oxygen, phosphorus, Group I metals, Group II metals, transition metals, olefinic groups, and aromatic groups. Due to the high impurity levels, additional processing can be required before the hydrocarbon products from non-catalytic hydrothermal processing can be used in conventional processes.

Feedstocks

In various embodiments of the invention, an algae feed or another biomass based feed can be processed using catalytic hydrothermal processing. In such embodiments, the feed can typically contain algae and water, and optionally can contain additional feed from another biocomponent source, where a biocomponent source is any source including and/or derived from biological material, such as from plants, animals, microbes, algae, or a combination thereof. Additionally or alternately, the feed can be a feed derived from a starting mixture containing algae and water, and can optionally contain feed from another biocomponent source. Further additionally or alternately, the feed can generally be a feed based on biomass.

It is noted that the water present in an algae (or other biomass) feed can include extracellular water and/or intracellular water. Intracellular water refers to water contained within the cell membrane of a cell, such as an algae cell. For an algae feed, a feed that appears relatively dry based on extracellular water content, can still contain a substantial portion of intracellular water. For algae whose cell walls have been ruptured (e.g., substantially dried/dewatered algae), the algae feed can only contain extracellular water (as ruptured cells do not have an inside, but only an outside). For an algae feed that contains intracellular water, computing the ratio of water to (dry) algae requires determining what portion of the algae weight is due to intracellular water, as the intracellular water should count toward the weight of water and not the weight of dry algae. As a clarifying example, an algae sample could include no extracellular water and still have a water to algae ratio of about 1:1 or greater, for example about 2:1 or greater, due to the amount of intracellular water in the algae. Thus, references herein to the weight of algae refer to the weight of dry algae, excluding intracellular water.

For a feed containing at least algae and water, the algae content of the feed can be at least about 5 wt %, for example at least about 10 wt %, at least about 20 wt %, at least about 25 wt %, or at least about 30 wt %. Additionally or alternately, the algae content of the feed can be about 50 wt % or less, for example about 30 wt % or less, about 25 wt % or less, or about 20 wt % or less. In terms of ratios, the ratio of water to algae in the feed can be at least about 1:1, for example at least about 2:1, at least about 3:1, or at least about 4:1. Additionally or alternately, the ratio of water to algae can be about 25:1 or less, for example about 20:1 or less or about 10:1 or less. In some embodiments, the algae content of the feed relative to the amount of water can be based on practical considerations regarding extraction of water from the source of the algae. Thus, in some embodiments, algae can be introduced into a reactor as a mixture or paste of algae and water. Additionally or alternately, a dried form of algae can be introduced into a reactor along with sufficient water, e.g., to reach a desired ratio of algae to water.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 80 wt % of lipids, based on total weight of the biomass itself.

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Nannochloropsis gaditiana, Tetraselmis chui, Tetraselmis tertiolecta, Dunaliella salina*, various species of *Chlorella*, and *Chlamydomonas reinhardtii*. Nonlimiting examples of additional or alternate algal sources include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species.

After catalytic hydrothermal processing, a portion of the products from catalytic hydrothermal processing can be combined with biocomponent and/or mineral based feeds. The combined feedstock can include varying amounts of feedstreams based on biocomponent sources. When desired, the feed can include at least about 0.1 wt % of feed based on a biocomponent source, for example at least about 0.5 wt %, at least about 1 wt %, at least about 3 wt %, at least about 10 wt %, at least about 15 wt %, at least about 25 wt %, at least about 50 wt %, or at least about 75 wt %. In such embodiments, the feed can additionally or alternately include about 100 wt % or less of biocomponent, for example about 90 wt % or less, about 75 wt % or less, or about 50 wt % or less. In other embodiments, the amount of biocomponent feed (e.g., for co-processing with the mineral oil portion of the feed) can be relatively small, for instance with a feed that includes at least about 0.5 wt % of feedstock based on a biocomponent source, e.g., at least about 1 wt %, at least about 2.5 wt %, or at least about 5 wt %, at least about 10 wt %, or at least about 20 wt %. In such embodiments, the feed can additionally or alternately include about 50 wt % or less of biocomponent based feedstock, for example about 25 wt % or less, about 20 wt % or less, about 10 wt % or less, or about 5 wt % or less.

In various embodiments of the invention, the combined feedstock can include feeds from various biomass or biocomponent sources, such as vegetable (higher plant), animal, fish, and/or algae. Generally, these biocomponent sources can include vegetable fats/oils, animal fats/oils, fish oils, pyrolysis oils, and algae lipids/oils, as well as components of such materials, and in some embodiments can specifically include one or more type of lipid compounds. Lipid compounds are typically biological compounds that are insoluble in water, but soluble in nonpolar (or fat) solvents. Non-limiting examples of such solvents include alcohols, ethers, chloroform, alkyl acetates, benzene, and combinations thereof.

Major classes of lipids include, but are not necessarily limited to, fatty acids, glycerol-derived lipids (including fats, oils and phospholipids), sphingosine-derived lipids (including ceramides, cerebrosides, gangliosides, and sphingomyelins), steroids and their derivatives, terpenes and their derivatives, fat-soluble vitamins, certain aromatic compounds, and long-chain alcohols and waxes.

In living organisms, lipids generally serve as the basis for cell membranes and as a form of fuel storage. Lipids can also be found conjugated with proteins or carbohydrates, such as in the form of lipoproteins and lipopolysaccharides.

Examples of vegetable oils that can be used in accordance with this invention include, but are not limited to rapeseed (canola) oil, soybean oil, coconut oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, tallow oil and rice bran oil.

Vegetable oils as referred to herein can also include processed vegetable oil material. Non-limiting examples of processed vegetable oil material include fatty acids and fatty acid alkyl esters. Alkyl esters typically include $C_1$-$C_5$ alkyl esters. One or more of methyl, ethyl, and propyl esters are preferred.

Examples of animal fats that can be used in accordance with the invention include, but are not limited to, beef fat (tallow), hog fat (lard), turkey fat, fish fat/oil, and chicken fat. The animal fats can be obtained from any suitable source including restaurants and meat production facilities.

Animal fats as referred to herein also include processed animal fat material. Non-limiting examples of processed animal fat material include fatty acids and fatty acid alkyl esters. Alkyl esters typically include $C_1$-$C_5$ alkyl esters. One or more of methyl, ethyl, and propyl esters are preferred.

Other biocomponent feeds usable in the present invention can include any of those which comprise primarily triglycerides and free fatty acids (FFAs). The triglycerides and FFAs typically contain aliphatic hydrocarbon chains in their structure having from 8 to 36 carbons, preferably from 10 to 26 carbons, for example from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the triglyceride present in the lipid material can be comprised of $C_{10}$ to $C_{26}$ fatty acid constituents, based on total triglyceride present in the lipid material. Further, a triglyceride is a molecule having a structure identical to the reaction product of glycerol and three fatty acids. Thus, although a triglyceride is described herein as being comprised of fatty acids, it should be understood that the fatty acid component does not necessarily contain a carboxylic acid hydrogen. In one embodiment, a majority of triglycerides present in the biocomponent feed can preferably be comprised of $C_{12}$ to $C_{18}$ fatty acid constituents, based on total triglyceride content. Other types of feed that are derived from biological raw material components can include fatty acid esters, such as fatty acid alkyl esters (e.g., FAME and/or FAEE).

Biocomponent based diesel boiling range feedstreams can have a wide range of nitrogen and/or sulfur contents. For example, a biocomponent based feedstream based on a vegetable oil source can contain up to about 300 wppm nitrogen. In contrast, a biomass based feedstream containing whole or ruptured algae can sometimes include a higher nitrogen content. Depending on the type of algae, the nitrogen content of an algae based feedstream can be at least about 2 wt %, for example at least about 3 wt %, at least about 5 wt %, or at least about 10 wt %, and algae with still higher nitrogen contents are known. The sulfur content of a biocomponent feed can also vary. In some embodiments, the sulfur content can be about 500 wppm or less, for example about 100 wppm or less, about 50 wppm or less, or about 10 wppm or less.

Aside from nitrogen and sulfur, oxygen can be another heteroatom component in biocomponent based feeds. A biocomponent diesel boiling range feedstream based on a vegetable oil, prior to hydrotreatment, can include up to about 10 wt % oxygen, for example up to about 12 wt % or up to about 14 wt %. Additionally or alternatively, such a biocomponent diesel boiling range feedstream can include at least about 1 wt % oxygen, for example at least about 2 wt %, at least about 3 wt %, at least about 4 wt %, at least about 5 wt %, at least about 6 wt %, or at least about 8 wt %. Further additionally or alternatively, a biocomponent feedstream, prior to hydrotreatment, can include an olefin content of at least about 3 wt %, for example at least about 5 wt % or at least about 10 wt %.

A mineral hydrocarbon feedstock refers to a conventional (e.g., non-biocomponent) hydrocarbon feedstock, typically derived from crude oil and that has optionally been subjected to one or more separation and/or other refining processes. In one preferred embodiment, the mineral hydrocarbon feedstock can be a petroleum feedstock boiling in the diesel range or above. Examples of suitable feedstocks can include, but are not limited to, virgin distillates, hydrotreated virgin distillates, kerosene, diesel boiling range feeds (such as hydrotreated diesel boiling range feeds), light cycle oils, atmospheric gasoils, and the like, and combinations thereof.

Mineral feedstreams for blending with a biocomponent feedstream can have a nitrogen content from about 50 wppm to about 2000 wppm nitrogen, for example from about 50 wppm to about 1500 wppm or from about 75 to about 1000 wppm. In some embodiments, the mineral feedstream can have a sulfur content from about 100 wppm to about 10,000 wppm sulfur, for example from about 200 wppm to about 5,000 wppm or from about 350 wppm to about 2,500 wppm. Additionally or alternatively, the combined (biocomponent plus mineral) feedstock can have a sulfur content of at least about 5 wppm, for example at least about 10 wppm, at least about 25 wppm, at least about 100 wppm, at least about 500 wppm, or at least about 1000 wppm. Further additionally or alternatively, the combined feedstock can have a sulfur content of about 2000 wppm or less, for example about 1000 wppm or less, about 500 wppm or less, about 100 wppm or less, or about 50 wppm or less. Still further additionally or alternatively, the nitrogen content of the combined feedstock can be about 1000 wppm or less, for example about 500 wppm or less, about 100 wppm or less, about 50 wppm or less, about 30 wppm or less, about 20 wppm or less, or about 10 wppm or less.

The content of sulfur, nitrogen, oxygen, and olefins in a feedstock created by blending two or more feedstocks can typically be determined using a weighted average based on the blended feeds. For example, a mineral feed and a biocomponent feed can be blended in a ratio of 80 wt % mineral feed and 20 wt % biocomponent feed. If the mineral feed has a sulfur content of about 1000 wppm, and the biocomponent feed has a sulfur content of about 10 wppm, the resulting blended feed could be expected to have a sulfur content of about 802 wppm.

Diesel boiling range feedstreams suitable for use in the present invention tend to boil within the range of about 215° F. (about 102° C.) to about 800° F. (about 427° C.). Preferably, the diesel boiling range feedstream has an initial boiling point of at least about 215° F. (about 102° C.), for example at least about 250° F. (about 121° C.), at least about 275° F. (about 135° C.), at least about 300° F. (about 149° C.), at least about 325° F. (about 163° C.), at least about 350° F. (about 177° C.), at least about 400° F. (about 204° C.), or at least about 451° F. (about 233° C.). Preferably, the diesel boiling range feedstream has a final boiling point of about 800° F. (about 427° C.) or less, or about 775° F. (about 413° C.) or less, or about 750° F. (about 399° C.) or less. In some embodiments, the diesel boiling range feedstream can have a boiling range from about 451° F. (about 233° C.) to about 800° C. (about 427° C.). Additionally or alternatively, the feedstock can be characterized by the boiling point required to boil a specified percentage of the feed. For example, the temperature required to boil at least 5 wt % of a feed is referred to as a "T5" boiling point. In one embodiment, the mineral oil feedstock can have a T5 boiling point of at least about 230° F. (about 110° C.), for example at least about 250° F. (about 121° C.) or at least about 275° F. (about 135° C.). Further additionally or alternatively, the mineral hydrocarbon feed can have a T95 boiling point of about 775° F. (about 418° C.) or less, for example about 750° F. (about 399° C.) or less or about 725° F. (about 385° C.) or less. In another embodiment, the diesel boiling range feedstream can also include kerosene range compounds to provide a feedstream with a boiling range from about 250° F. (about 121° C.) to about 800° F. (about 427° C.).

Hydrothermal Processing Conditions

In various embodiments, catalytic hydrothermal processing can be performed in a batch, semi-batch, and/or continuous type processing environment(s). Regardless of whether the reaction takes place in a batch, semi-batch, or continuous reaction system, any system region where the biomass is treated under hydrothermal treatment conditions can be referred to as the reaction zone. The reaction zone can correspond to a reactor for a batch or semi-batch environment and/or to a reactor, conduit, or other location for hydrothermal treatment in a continuous reaction system.

In embodiments involving a batch reactor, the reactor can be any type of batch reactor suitable for handling the processing conditions. Due to the potential presence of water at supercritical conditions, stainless steel can be a suitable non-reactive material for the reactor walls. Other materials and/or coatings for the reactor surfaces can be used that are compatible with the reaction conditions described herein. Examples of suitable reactors can include, but are not limited to, autoclaves, stirred tanks, plough mixers, and the like, and combinations thereof. Alternately, a bubble column could be used. One possible advantage for batch or semi-batch type processing can occur for algae feeds that have relatively poor flow characteristics. For example, at an algae concentration relative to water of about 20 wt % (i.e., about 4 parts water to 1 part algae by weight), the resulting mixture can have the consistency of a paste. Such a paste could be difficult to move, e.g., using pumps in a continuous flow type reactor.

In one embodiment, a batch reactor can be used for catalytic hydrothermal processing of an algae feed. A portion of algae feed mixed with water can be introduced into the reactor, which can then be purged (if necessary), e.g., to remove any oxygen containing gases. Additionally or alternately, a catalyst can also be introduced into the reactor. The catalyst can be included as part of the mixture of algae and water, or the catalyst can be introduced into the reactor as part of a separate input. Additionally or alternately, a partial pressure of an inert gas and/or a reducing gas can then be introduced into the reactor. Examples of suitable reducing gases can include hydrogen, while suitable inert gases can include nitrogen. Additional or alternate examples of suitable reducing gases can include any gas that does not add molecular oxygen to the reaction atmosphere, whether prior to the start of the reaction or from dissociation forming oxygen during the hydrothermal processing. The partial pressure of additional gas introduced into the reactor, when present, can be at least about 1 bar (about 0.1 MPa), for example at least about 25 bar (about 2.5 MPa), at least about 40 bar (about 4.0 MPa), or at least about 50 bar (about 5.0 MPa). Additionally or alternately, the partial pressure of gas introduced into the reactor, when present, can be about 100 bar (about 10 MPa) or less, for example about 75 bar (about 7.5 MPa) or less or about 50 bar (about 5.0 MPa) or less. Note that introducing a reducing gas can correspond to at least partially dissolving a reducing gas in the water (e.g., saturating the water) for the hydrothermal treatment.

After introducing the algae, water, catalyst, and any additional reducing and/or inert gases, the batch reactor can be sealed. The temperature of the reactor can then be raised to at least about 50° C., for example at least about 80° C., at least about 100° C., at least about 150° C., at least about 200° C., at least about 250° C., at least about 275° C., or at least about 300° C. Additionally or alternately, the temperature of the reactor can be raised to about 500° C. or less, for example about 400° C. or less, about 380° C. or less, about 350° C. or less, about 300° C. or less, or about 275° C. or less. Further additionally or alternatively, the pressure in the reactor can be at least about 1 barg (about 0.1 MPag), for example at least about 4.5 barg (about 450 kPag), at least about 25 barg (about 2.5 MPag), at least about 40 barg (about 4.0 MPag), at least about 50 barg (about 5.0 MPag), or at least about 100 barg (about 10 MPag). Additionally or alternately, the partial pressure of gas introduced into the reactor, when present, can be about 300 barg (about 30 MPag) or less, for example about 250 barg (about 25 MPag) or less, about 225 barg (about 22.5 MPag) or less, or about 200 barg (about 20 MPag) or less.

In some embodiments, the combination of pressure and temperature within the reactor can be selected so that the water in the reactor substantially does not undergo a phase change (e.g., completely does not undergo a phase change). In a phase diagram for water, the critical point is located at a temperature of about 374° C. and a pressure of about 22 MPa. At temperature and pressure combinations beyond this point in the phase diagram, water does not experience a phase transition between a liquid phase and a gaseous phase. Instead, beyond the critical point, water behaves as a single fluid phase. Thus, in some embodiments, the combination of pressure and temperature can be selected so that the liquid water in the reactor remains the stable phase until conditions beyond the critical point are achieved. One way of satisfying this condition can be to select reaction temperatures and pressures that are less than the critical point and thus that do not lead to a phase transition. Note that in some embodiments, a partial pressure of additional gas can be introduced into the reactor (in which case, some minimal amount of water may become vapor, but this situation is contemplated in the invention not to be a "substantial" phase change). If the partial pressure of additional gas is greater than about 22 MPa, then the pressure is already beyond the critical point for water and substantially no phase transition is possible. Note also that, in a closed reactor, e.g., which can have a partial pressure of another gas, substantial phase transitions of water are not likely to occur, so long as the volume of liquid water is sufficient relative to the volume of the reactor.

Additionally or alternately, the pressure within a reactor can be set by selecting a temperature for the water. In some embodiments, the reactor can be sealed or closed after introduction of water and any additional gases, if present. A partial pressure of water vapor should develop in the reactor to correspond to the temperature of the water in the reactor. As the temperature of the reactor increases, a corresponding higher partial pressure of water should develop in the reactor. The hydrothermal processing can be performed at a pressure that represents the combination of the partial pressure of water at the reaction temperature and the partial pressure of any additional inert and/or reducing gases, as well as the partial pressure of any gases generated or evolved during processing. Examples of water partial pressures at various temperatures can include about 0.01 MPa at about 50° C.; about 0.05 MPa at about 80° C.; about 0.1 MPa at about 100° C.; about 0.5 MPa at about 150° C.; about 1.6 MPa at about 200° C.; about 4.0 MPa at about 250° C.; about 5.9 MPa at about 275° C.; about 8.6 MPa at about 300° C.; about 16.5 MPa at about 350° C.; and about 22.1 MPa at about 374° C. Because about 22.1 MPa and about 374° C. corresponds to the critical point in the phase diagram for water, it is not meaningful to refer to the partial pressure of "water vapor" in a reactor at temperatures beyond that point.

In some embodiments, the hydrothermal processing can be performed in a continuous flow type reactor. An example of a continuous flow type reactor can be a pipe or other conduit that can be heated to raise the temperature of the feed in the conduit to the desired hydrothermal processing temperature. For example, a conduit passing through a furnace could be used, and/or a conduit surrounded by steam. The conduit can have any convenient shape for passing through the heating zone. For example, a conduit having the shape of a spiral can be used to increase the size of the portion of the conduit within the heating zone.

It has been noted that the amount of water needed in order to perform hydrothermal processing may not be sufficient to provide the type of flow characteristics desired for a continuous flow environment. In a continuous flow processing environment, one option for improving the fluid flow characteristics of the algae can be to increase the water content of the algae feed. However, increasing the water content can also result in a corresponding decrease in the yield per volume of the reaction system, due to the reduction in the amount of algae in the feed.

Figure 1:
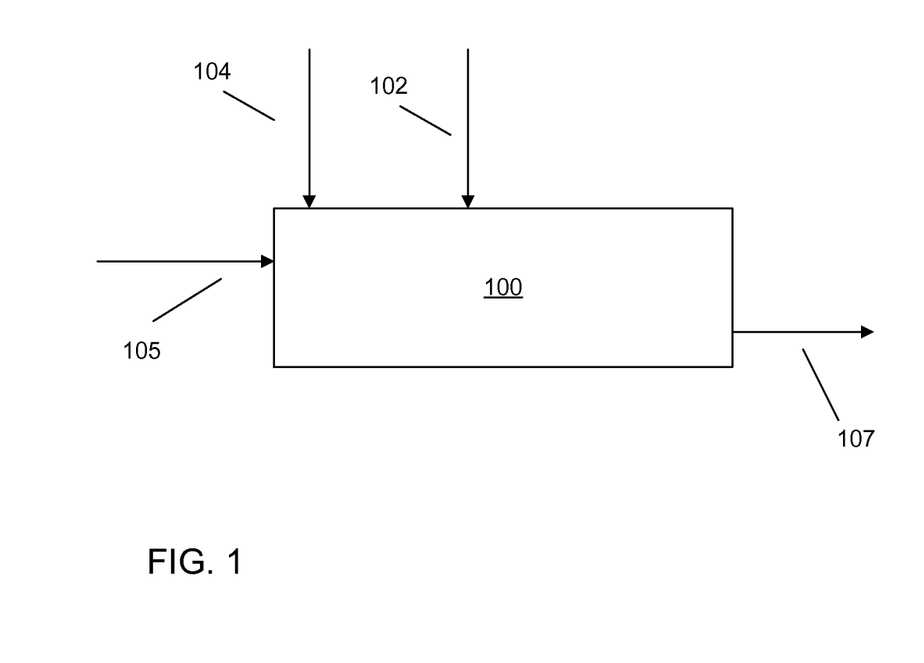
FIG. 1 depicts a reaction system suitable for performing a process according to an embodiment of the invention.

FIG. 1 schematically shows an example of a reactor suitable for use in an embodiment of the invention. In FIG. 1, hydrothermal processing reactor 100 can represent any type of reactor suitable for performing a catalytic hydrothermal process for treatment of an algae (or other biomass) feed. Input flows into reactor 100 can include a gas input 102, such as an inert gas input, a hydrogen gas input, another type of reducing gas input, or a combination thereof. Another input flow can be an algae or biomass input 104. If algae input 104 has poor flow properties, such as due to a sufficiently low water content, algae input 104 may alternately represent a non-flow input, such as extrusion, pouring, or dumping of the algae input 104 into reactor 100. Optionally, a supplemental input flow 105 can be provided for various reasons. One option for a supplemental input flow 105 can be to include additional water, so that hydrothermal processing conditions can be maintained. An additional or alternate component for supplemental input flow 105 can be an "inert" hydrocarbon stream (that can undergo minimal reaction under hydrothermal processing conditions) and/or a product recycle stream. Such a hydrocarbon stream and/or recycle stream could be used as a carrier for a catalyst or a catalyst precursor. As an alternative, algae input 104 and supplemental input 105 can be combined into a single stream prior to entering the reactor 100. The hydrothermal treatment can generate an output flow 107, e.g., which can be a mixture of various phases. Phases that can comprise output flow 107 can include a gas phase, a hydrocarbon based phase, an aqueous based phase, and one or more solid phases. These phases may optionally be mixed with each other, such as mixing of the solids with the aqueous phase.

Catalyst for Catalytic Hydrothermal Processing

Another option during processing can be the use of a hydrothermal processing catalyst. A hydrothermal processing catalyst can be in a form that is soluble in the hydrothermal reaction environment (or in at least one feed introduced thereinto), or the catalyst can be in the form of catalyst particles in the hydrothermal reaction environment. Catalyst particles in the reaction environment can have any suitable particle size and/or particle size distribution. The catalyst particles can optionally be a supported catalyst, with a catalytic material supported on a substrate.

In an embodiment involving a catalyst that is soluble in the hydrothermal reaction environment, the catalyst can be introduced into the reaction either as a catalyst or a catalyst precursor. The soluble catalyst can be soluble in water or in another solvent introduced into the hydrothermal reaction environment. Examples of solvents can include but are not limited to alcohols, acids, hydrocarbons, or other oils. Additionally or alternately, the solvent can correspond to a product that is generated by the hydrothermal treatment process. Examples of suitable catalysts or catalyst precursors can include, but are not limited to, transition metal salts such as metal acetates, metal carbonates, metal acetyl acetonates, or combinations thereof. Examples of suitable metals for such metal salts can include, but are not limited to, Cr, V, Mo, Ni, Cu, Fe, Co, Mn, and a combination thereof. Additionally or alternately, a suitable metal can include a Group VIB metal or a Group VIII metal, or a combination of one or more Group VIB metals and one or more Group VIII non-noble metals. Further additionally or alternately, a catalyst precursor can be activated to form a metal sulfide by introducing a sulfur-containing stream into the reaction environment, such as a stream of $H_2S$.

Relative to the amount of algae, the amount of metal in a soluble catalyst or catalyst precursor in the reactor (reaction zone) can be at least about 0.01 wt % (100 wppm), for example at least about 0.05 wt %, at least about 0.1 wt %, at least about 0.25 wt %, or at least about 0.5 wt %. Additionally or alternately, the amount of catalyst in the reactor (reaction zone) can be about 5.0 wt % or less relative to the amount of algae, for example about 3.0 wt % or less, about 2.0 wt % or less, about 1.0 wt % or less, about 0.5 wt % or less, or about 0.25 wt % or less.

Aside from the soluble catalyst option, a supported catalyst can be used including a noble metal (e.g., Pt, Pd, Rh, Ru, Ir, or a combination thereof). Additionally or alternately, the support for the catalyst can be a hydrothermally stable support. Examples of suitable supports can include, but are not limited to, refractory oxides such as titania and/or zirconia; silica; activated carbon; carbon on which is deposited one or more metals selected from titanium, zirconium, vanadium, molybdenum, manganese, and cerium; magnesium oxides; hydrotalcites; other various types of clays; and combinations thereof, such as a mixture of two or more of titania, zirconia, and silica. Additionally or alternately, the support material can be substantially free of alumina. As used herein, "substantially free" of alumina should be understood to mean less than 1 wt % alumina, preferably less than 0.1 wt % alumina, for example less than 0.01 wt % of alumina, completely no added alumina, or completely no alumina.

Still another catalyst option can be to use a basic metal or mixed metal oxide with or without a noble metal. Examples of such catalysts without a noble metal can include, but are not limited to, magnesium oxide, hydrotalcites, potassium supported on titania and/or zirconia, and combinations thereof.

Yet another catalyst option can be to use hydroprocessing type metals supported on a suitable support. Examples of hydroprocessing type metals can include, but are not limited to, a combination of a Group VIII metal (such as Co and/or Ni) with a Group VIB metal (such as Mo and/or W). Combinations of three or more Group VIII and/or Group VI metals can additionally or alternately be used (e.g., NiMoW, CoNiMo, CoMoW, and the like). Suitable support materials include those identified hereinabove.

Yet another catalyst option can be to select a catalyst that includes biocompatible materials. For example, a biocompatible material can be a material that can serve as a nutrient for growth of biomass, such as algae, and/or a material that does not harm a biomass growth environment at the concentrations of the material used for the hydrothermal treatment. A biocompatible catalyst can optionally include a biocompatible support. Examples of suitable metals in biocompatible catalysts can include K, Na, Mg, Ca, Fe, Zn, Mn, Mo, Cu, and combinations thereof. The biocompatible catalysts can be in the form of a hydroxide, oxide, carbonate, or an organometallic derivative such as an acetate or acetylacetonate (acac). Additionally or alternately, the catalyst can be impregnated on a support such as activated carbon. The biomass being processed, such as algae, can alternatively serve as a support for the catalyst. In some embodiments, these biocompatible catalyst materials can be recycled either as a nutrient feed for biomass growth or as an input into the hydrothermal treatment reaction.

Relative to the amount of algae, the amount of catalyst in the reactor (reaction zone) can be at least about 0.05 wt %, for example at least about 0.1 wt %, at least about 1 wt %, at least about 2.5 wt %, or at least about 5 wt %. Additionally or alternately, the amount of catalyst in the reactor (reaction zone) can be about 20 wt % or less relative to the amount of algae, for example about 15 wt % or less or about 10 wt % or less.

The amount of metal supported on the catalyst can be varied. Relative to the weight of the catalyst, the amount of noble metal supported on the catalyst, when present, can be at least about 0.1 wt %, for example at least about 0.5 wt %, at least about 0.6 wt %, at least about 0.75 wt %, or at least about 1.0 wt %, based on the total catalyst weight. Additionally or alternatively, the amount of noble metal supported on the catalyst, when present, can be about 1.5 wt % or less, for example about 1.0 wt % or less, about 0.75 wt % or less, or about 0.6 wt % or less, based on the total catalyst weight. More generally, the amount of metal(s), individually or in mixtures, on the catalyst support can be at least about 0.1 wt %, for example at least about 0.25 wt %, at least about 0.5 wt %, at least about 0.6 wt %, at least about 0.75 wt %, at least about 1 wt %, at least about 2.5 wt %, or at least about 5 wt %, based on the total catalyst weight. Additionally or alternatively, the amount of metal(s), individually or in mixtures, on the catalyst support can be about 35 wt % or less, for example about 20 wt % or less, about 15 wt % or less, about 10 wt % or less, or about 5 wt % or less, based on the total catalyst weight.

Use of a catalyst can present additional issues for hydrothermal processing. For a catalyst or catalyst precursor that is initially soluble in the reaction environment, one issue can be separation of the catalyst from the reaction products. One separation method can be filtration. If the catalyst is not soluble in the reaction products, the resulting catalyst particles can be filtered out of the product with which the catalyst particles are mixed. One reason the catalyst may be insoluble in the reaction products is if the catalyst has been converted to another form, such as conversion of a catalyst precursor to a metal sulfide.

Supported (or particulate) catalysts can also present additional considerations. Additionally or alternatively, the particle size for the catalyst particles can be varied, e.g., selected to facilitate separation of the catalyst particles from other solids. In such an embodiment, the catalyst particles can have an average particle size of at least about 1000 µm, for example at least about 1500 µm or at least about 2000 µm. To achieve a desired catalyst particle size, catalysts can optionally be formulated to include a hydrothermally stable binder material, in addition to the support material and any active metals, if present. Suitable hydrothermally stable binder materials can be similar to materials used as a support material and/or can include, but are not necessarily limited to, an oxide of one or more metals selected from silicon, titanium, zirconium, vanadium, molybdenum, manganese, and cerium. For a supported catalyst that is formulated with a binder, the support material can function as a binder, or a different material can be used as a binder.

Supported catalysts can be contacted with a feed under hydrothermal processing conditions using a variety of reactor types. Batch or semi-batch reactors as described above can be used with a particulate catalyst. For example, the catalyst can be added to such reactors when the algae, water, and other optional gases are added to the reactor. A continuous flow conduit can additionally or alternatively be used. In this type of embodiment, the flow through the conduit may resemble a slurry of catalyst particles suspended in the flow of algae and water.

In addition to the reactors suitable for non-catalytic treatment, other types of continuous flow reactors can potentially be used for hydrothermal treatment of an algae feed, such as a fixed bed reactor, a moving bed, an ebullating bed reactor, or the like. If a fixed bed reactor is used, one concern could be fouling of the catalyst bed, e.g., due to solids present in the biomass or algae feed. Fouling of a catalyst bed can result in a higher than expected pressure drop across a catalyst bed, due to restrictions in flow of feed through the bed. Fixed bed reactors can often handle feeds with particle sizes up to about 150 µm without significant fouling issues. Nevertheless, any fouling of a catalyst bed can be somewhat mitigated, e.g., by having bypass tubes to control the pressure drop across the catalyst bed. Unfortunately, although individual algae cells have small diameters, relative to 150 µm, hydrothermally treated algae can have an increased tendency to agglomerate. As a result, 5% or more of the algae based solids resulting from hydrothermal treatment of an algae feed can be in the form of agglomerated particles with a particle size greater than 150 µm. Nevertheless, in some embodiments, a fixed bed reactor may be used, particularly when agglomerative behavior of the product algae solids can be mitigated, e.g., by using a sufficient space velocity and/or through other means.

As an alternative to a fixed bed reactor, an ebullating bed reactor can be used for hydrothermal processing. In a conventional ebullating bed reactor, both the feedstock (water and algae) and a treat gas (hydrogen-containing reducing gas) can be introduced into the reactor from the bottom of the reactor. In such reactors, a recycled feed containing a portion of the reactor effluent can also be introduced into the bottom of the reactor. These feed flows can travel up into the reactor and pass through a catalyst support grid designed to prevent catalyst from entering the areas at the bottom of the reactor where the feed pumps are located. The catalyst in such ebullating bed reactors is typically located above the catalyst support grid.

When the feedstock (and optionally additional gas) flow(s) reach the catalyst bed, the bed generally becomes fluidized, leading to expansion of the bed as well as mixing within the bed. The feed (and hydrogen) can react within the bed to form products, including liquid products, solid products, and gaseous products. The flow in a conventional ebullating bed reactor can continue upward until an effluent is drawn off at the top. This effluent can be a combination of desired products, unreacted hydrogen (when present), and byproduct gases, including contaminant gases such as $H_2S$ or $NH_3$ that may have formed during the reaction. In preferred embodiments, a portion of the liquid effluent can be recycled, e.g., to the bottom of the reactor. If desired, the gases can be separated from the liquid portion of the effluent.

Phosphorus Content in Solids Fraction

Additionally or alternatively to recovery of a hydrocarbon product, recovery of other algae solids (or other biomass solids) can be beneficial. For example, phosphorus can be recovered from the residual algae solids after hydrothermal treatment. One potential use for recovered phosphorus can be as a nutrient for growth of additional algae or other biomass.

Improving the recovery of phosphorus from hydrothermal processing of biomass can involve balancing several factors. One benefit of various embodiments can be that phosphorus forms a solid product, e.g., that can be filtered out from the liquid product streams. Any phosphorus that remains as part of the liquid hydrocarbon product and/or any phosphorus that becomes solublized in a solvent could be recovered in one or more separate, additional processes. In the discussion below, the recovery of phosphorus from products of hydrothermal treatment can be evaluated based on the amount of phosphorus recovered as solids.

Because the recovery of phosphorus can be evaluated based on the amount of phosphorus in the solids product, an initial goal can be to develop processing conditions that result in a large percentage of phosphorus in the solids product. One conventional way of processing a biomass feed, such as an algae feed, can be to extract a desired hydrocarbon product from the feed using an extraction solvent (e.g., such as a mixture of $CHCl_3$ and $CH_3OH$). An extraction solvent can advantageously produce yields of phosphorus in the solids product of greater than 90 wt % relative to the amount of phosphorus in the feed. For an efficient phosphorus recovery process, it can be desirable to have a phosphorus yield in the solids product, relative to the feed phosphorus content, of at least 80 wt %, for example at least 85 wt % or at least 90 wt %.

One option for improving the yield of phosphorus in the solids product can be to increase the amount multivalent cations in the hydrothermal reaction. Many biomass feeds can contain at least some multivalent cations, such as Ca, Mg, and/or Fe. These multivalent cations can form phosphates or other phosphorus solids as part of the solids product. For some feeds, increasing the amount of available multivalent cations may increase the amount of phosphorus in the solids product, such as by adding extra cations selected from Ca, Mg, Fe, Al, or a combination thereof. In some such embodiments, sufficient multivalent cations can be added to provide at least about a 1:1 molar ratio of multivalent cations to phosphorus atoms. This can correspond to adding at least about 0.1 wt %, for example at least about 0.2 wt % or at least about 0.3 wt % of a multivalent metal. Additionally or alternately, the amount of added multivalent metal can be about 1.0 wt % or less, for example about 0.8 wt % or less, about 0.6 wt % or less, about 0.5 wt % or less. Note that the amount of multivalent metal can be reduced in a feed that already contains some multivalent metal.

Another consideration in selecting conditions for hydrothermal processing can be the relative amount of phosphorus in the solids product. As noted above, solvent extraction can produce a solids product that has greater than 90 wt % of the initial phosphorus in the feed. Unfortunately, such conventional solvent processing can also result in a relatively large amount of carbonaceous solids, e.g., in which product phosphorus can be present in amounts as low as 5 wt % or below. This can present a number of problems. First, additional processing can be required to extract the phosphorus from the much larger proportion of carbon solids and/or other solids. Another problem can be that relatively high carbon content in the solids product can increase the difficulty of using/selling the solids for an economically valuable purpose. To say it another way, a large proportion of carbon in the solids product can mean that a noticeable amount of carbon may be lost, rather than being converted into a desired product.

The amount of phosphorus recovered in the solids product relative to carbon can depend in part on the reaction conditions. Without being bound by any particular theory, it is believed that relatively low severity reaction conditions can lead to incomplete reaction of the biomass feed. This can result in algae (or other biomass) solids that are unreacted and/or only partially reacted. The algae is initially solid, so unreacted and/or partially reacted algae can still be a solid after an incomplete reaction. The unreacted and/or partially reacted algae can thus add to the carbon content of the solids product, which can therefore reduce the ratio of phosphorus to carbon. It is noted that incomplete reaction may additionally or alternately lead to a reduction in the amount of phosphorus in the solids relative to the initial amount of phosphorus.

Also without being bound by theory, it is believed that reaction conditions that are too severe may lead to increased carbon in the solids product. Hydrothermal processing of biomass feeds can lead to increased production of some heavier molecules, including aromatics. A portion of these heavier molecules can correspond to insoluble compounds that tend to form solids. These additional solids can thus contribute to lowering the ratio of phosphorus to carbon in the solids products.

In some embodiments, the hydrothermal processing temperature can be selected to improve the ratio of phosphorus to carbon in the solids product. For example, the reaction temperature can, in on embodiment, range from about 275° C. to about 325° C. Additionally or alternately in catalytic hydrothermal processing embodiments, the presence of catalyst can reduce the processing temperature that leads to an increase in the ratio of phosphorus to carbon in the solids product. In such embodiments, the reaction temperature can range from about 250° C. to about 300° C.

Additionally or alternately, improving the ratio of phosphorus to carbon in the solids product for hydrothermal processing, either in the presence or absence of a catalyst, can be based on a combination of processing temperature and reaction time. For example, for a processing time of about 60 minutes to about 105 minutes, the reaction temperature can be about 250° C. to about 300° C. For a processing time of about 45 minutes to about 90 minutes, the reaction temperature can be about 275° C. to about 325° C. For a processing time of about 30 minutes to about 60 minutes, the reaction temperature can be about 285° C. to about 335° C. For a processing time of about 24 minutes to about 48 minutes, the reaction temperature can be about 300° C. to about 350° C. For a processing time of about 15 minutes to about 30 minutes, the reaction temperature can be about 325° C. to about 375° C. For a processing time of about 6 minutes to about 24 minutes, the reaction temperature can be about 350° C. to about 400° C.

Further additionally or alternately, improving the ratio of phosphorus to carbon in the solids product for catalytic hydrothermal processing can be based on a combination of processing temperature and reaction time. For example, for a processing time from about 60 minutes to about 105 minutes, the reaction temperature can be from about 225° C. to about 275° C.; for a processing time from about 45 minutes to about 90 minutes, the reaction temperature can be from about 250° C. to about 300° C.; for a processing time from about 30 minutes to about 60 minutes, the reaction temperature can be from about 275° C. to about 325° C.; for a processing time from about 24 minutes to about 48 minutes, the reaction temperature can be from about 285° C. to about 335° C.; for a processing time from about 15 minutes to about 30 minutes, the reaction temperature can be from about 300° C. to about 350° C.; and for a processing time from about 6 minutes to about 24 minutes, the reaction temperature can be from about 325° C. to about 375° C. It is noted that, in a continuous reaction environment, a reaction time can more accurately be described in terms of a residence time or a space velocity.

Separation of Products from Catalytic Hydrothermal Processing

Hydrothermal processing can result in a multi-phase product. The multi-phase product can include a gas phase, a hydrocarbon or oil phase, and an aqueous phase that can include solids. The gas phase, oil phase, aqueous phase, and solids phase can be separated from each other by any convenient method, such as by use of a three phase separator. Characterization of the oil phase is described further below. In some embodiments, the solids phase can initially be together with aqueous phase. For example, the solids phase can be suspended in the aqueous phase or can be a precipitate slurried in and/or settling out of the aqueous phase. The solids phase can also be valuable, containing one or more of: phosphorus and other potential nutrients for algae and/or other microorganisms; unreacted and/or only partially reacted biomass; and optionally catalyst particles if the process is a catalytic hydrothermal process; inter alia. In some embodiments, the catalyst particles can be separated from the other solids to allow for their recycle, as well as for recycle of the nutrients, if present.

Figure 2:
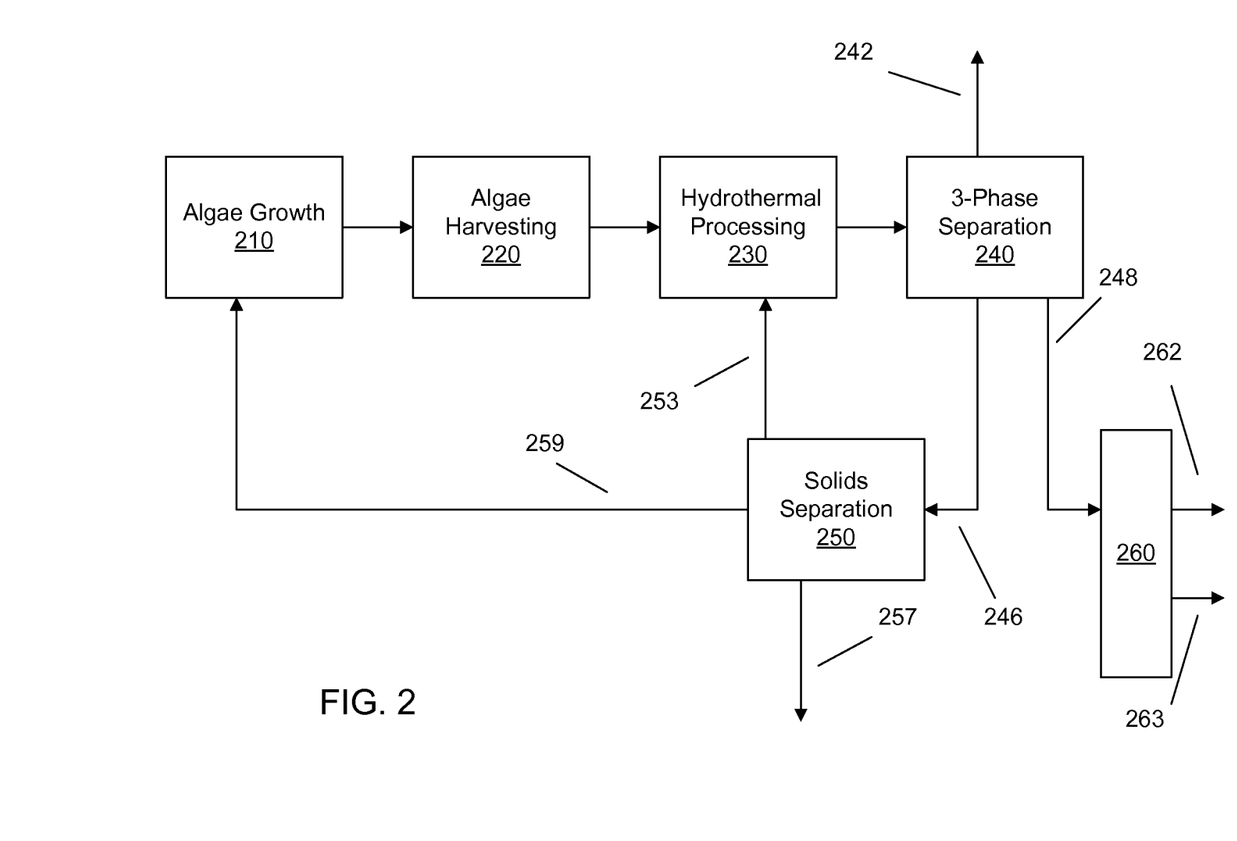
FIG. 2 schematically shows a reaction scheme according to an embodiment of the invention.

FIG. 2 shows a schematic example of a processing flow for an embodiment of the invention involving algae as the form of biomass for processing. In FIG. 2, an integrated scheme is shown where products from the (optionally catalytic) hydrothermal processing are recycled for further use. In FIG. 2, the biomass input for the hydrothermal processing can be from an algae source. This algae can be produced by an algae growth process 210, which can include any convenient and/or known process. The algae can be harvested 220 for conversion into hydrocarbon products. As part of algae harvesting 220, some amount of water can optionally be removed from the algae. For example, water can be completely removed from the algae as part of production of freeze-dried algae. Alternately, water can be removed using only physical processes, such as by centrifuge, which can advantageously result in an algae feed with a water to algae weight ratio of about 10:1 or less, for example about 7.5:1 or less, or about 5:1 or less. Additionally or alternately, the water to algae weight ratio can be at least about 2:1, for example at least about 2.5:1, or at least about 3:1. One advantage of performing only a partial separation of algae and water can be that less energy is needed to perform only a partial separation, as compared to complete separation.

After harvesting, the harvested algae can be used as a feed for hydrothermal processing 230. The algae feed can be optionally combined with a catalyst, a partial pressure of gas such as hydrogen, and optionally water, e.g., if sufficient water is not included with the algae feed. The hydrothermal processing 230 can generate a variety of products. An initial separation of these products can be performed in three-phase separator 240. Three-phase separator 240 can be used to generate a gas phase product 242, a hydrocarbon or oil product 248, and a product including water and various solids 246. The gas phase product 242 can include hydrogen, inert gases that may have been present during hydrothermal processing 230, product gases from the hydrothermal processing 230 (such as $CO_2$, CO, $H_2S$, $NH_3$, and the like, and combinations thereof), and low boiling hydrocarbons produced during catalytic hydrothermal processing 230. The low boiling hydrocarbons can include hydrocarbons that are gases at room temperature (such as methane, ethane, or the like, or combinations thereof) and/or hydrocarbons that are gases at the temperature of the three-phase separation. If the three-phase separation is performed at an elevated temperature, this could include higher boiling aliphatic hydrocarbons and/or other species (such as methanol). Note that some of the above products may be at least partially solublized in the water phase, such as the product gases from the hydrothermal processing.

In the products from hydrothermal processing 230, the desired hydrocarbon or oil product can form a phase separate from an aqueous phase containing various solids. These distinct phases can be separated in three-phase separation 240. The resulting hydrocarbon product 248 can represent the desired oil product from the catalytic hydrothermal treatment. The hydrocarbon product 248 may, if desired, undergo a variety of additional processing, which can include an optional distillation 260 to isolate desired boiling ranges 262 and 263 of the product and/or hydroprocessing to upgrade the hydrocarbon product 248 or a distillation cut 262 or 263 for use. Additionally or alternately, at least a portion of hydrocarbon product 248 and/or of distillation cut(s) 262 and/or 263 may optionally be recycled to hydrothermal processing 230, e.g., for combination with the algae/water input feed, which may improve the input feed flow characteristics.

In some embodiments, the water and solids 246 from the three-phase separation 240 can include several types of solids, which can include but are not limited to solids derived from the algae, solids comprising phosphorus and/or various metals, unreacted and/or partially reacted biomass, and optionally catalyst particles, including spent catalyst particles. The water and solids 246 can be further processed in solids separation 250 to separate the solids for further use. Solids separation 250 can generate an aqueous stream 257, optional catalyst particles 253, and algae-derived solids 259. Note that separation of the optional catalyst particles from the algae-derived solids may occur prior to separation of the aqueous phase from the solids. In a preferred embodiment, the optional catalyst particles 253 can be returned to the catalytic hydrothermal processing for further use. Additionally or alternately, the algae-derived solids 259 can be returned to the algae growth process 210, e.g., as raw material for developing a new batch of algae feed. Further additionally or alternately, at least a portion of aqueous stream 257 and/or of the water from water and solids 246 can be recycled to the algae growth process 210, e.g., to provide additional nutrients such as nitrogenated species (like $NH_3$).

Although the scheme in FIG. 2 implies a series of processes located together, the algae growth 210 and harvesting 220 could take place at a location remote from the catalytic hydrothermal processing 230. In such an embodiment, several of the arrows in FIG. 2 could represent transport steps, such as transport of the harvested algae to the location for catalytic hydrothermal processing and transport of the algae-derived solids to the algae growth site.

Processing of Product Solids for Recycle of Nutrients

As noted above, some of the product solids can be recycled for use as nutrients for growth of further algae or other biomass. An example of this type of recycle can be recycling of phosphorus compounds. In order to recycle the phosphorus, the phosphorus can be converted from the solid form into a precursor form that can be readily processed into a suitable nutrient. An example of this type of conversion can be conversion of phosphorus in the product solids into a more easily distributable form, such as phosphoric acid. The phosphoric acid can then be used either as a nutrient, or as a precursor or reagent to make a suitable nutrient.

Phosphorus can be contained in the product solids in a variety of forms, such as phosphates and/or phosphites, and may be coordinated by Ca, Mg, or other multivalent cations. The solids can also contain carbon compounds. In order to separate the phosphorus from the carbon, the phosphorus in the solids can, in one embodiment, be converted to phosphoric acid. Conversion of phosphorus to phosphoric acid is a known reaction, and can be performed by treating the phosphorus containing solids with sulfuric acid. The sulfuric acid can react with the phosphorus to form phosphoric acid. The sulfate ions from the sulfuric acid can combine with Ca or Mg cations and precipitate out. In such situations, the carbon may remain as additional solid product. The sulfate solids and carbon can be separated from the phosphoric acid by physical and/or known/conventional means, e.g., using filtration or a settling pond.

Evaluation of Products from Hydrothermal Processing

Hydrothermal processing can be used to extract various hydrocarbon fractions from an algae (or other biomass) feed. One example of a hydrocarbon fraction that can be extracted from an algae feed can include and/or be a distillate fraction. In the discussion below, a distillate fraction refers to a fraction that has a boiling range between about 193° C. and about 360° C., or alternately to a fraction having at least 90 wt % of its boiling range between about 193° C. and about 360° C. (e.g., the T5 could be about 193° C. and the T95 about 360° C., or the T2 could be about 193° C. and the T98 about 360° C., or the like).

One way to evaluate the products of a hydrothermal treatment process, whether catalytic or non-catalytic, can be to consider the hydrocarbon yield from the process. A total yield can be defined for a hydrothermal treatment process based on the weight of hydrocarbon product captured relative to the initial weight of the algae or other biomass. A distillate yield can also be defined for a hydrothermal treatment process. One yield characterization can be the total distillate boiling range yield for a process relative to the starting weight of algae or biomass. Another characterization can be the percentage of distillate produced relative to the total hydrocarbon yield.

An additional or alternate way to evaluate the products of a hydrothermal treatment process can be based on the levels of various impurities in the products. In a non-catalytic hydrothermal treatment process (or in a catalytic hydrothermal process, analyzed on a catalyst-free basis), the hydrocarbon products can tend to incorporate impurities such as nitrogen, oxygen, carbon-carbon double bonds, and aromatic groups. Thus, the percentage of heteroatoms (nitrogen and/or oxygen) in the total hydrocarbon product and/or the distillate product can be of interest. The percentage of carbon-carbon double bonds and aromatic groups can be measured using techniques such as $^{13}C$ NMR, and/or other metrics can be used such as the ratio of hydrogen to carbon in the products.

ADDITIONAL EMBODIMENTS

Additionally or alternatively, the present invention can include one or more of the following embodiments.

Embodiment 1

A method for hydrothermally processing biomass, comprising: introducing a biomass feed having a water to biomass ratio of at least 1:1 into a reaction zone, the biomass feed having a phosphorus content; hydrothermally treating the biomass feed under effective hydrothermal treatment conditions to produce a multi-phase product, the multi-phase product including a solids portion containing at least about 80% of the phosphorus content of the biomass feed; and separating the multi-phase product to produce at least a gas phase portion, a liquid hydrocarbon product, and the solids portion.

Embodiment 2

A method for hydrothermally processing biomass, comprising: adding a multivalent metal to a biomass feed having a phosphorus content; contacting the biomass feed with water in the presence of the multivalent metal under effective hydrothermal treatment conditions to produce a multi-phase product, the multi-phase product including a solids portion containing at least about 80% of the phosphorus content of the biomass feed; and separating the multi-phase product to produce at least a gas phase portion, a liquid hydrocarbon product, and the solids portion.

Embodiment 3

The method of embodiment 2, wherein the multivalent metal comprises Ca, Mg, Fe, or a combination thereof, for example comprises Ca and/or Mg.

Embodiment 4

The method of embodiment 2 or embodiment 3, wherein the multivalent metal is added to the biomass feed in a reaction zone for the contacting of the biomass feed with water under effective hydrothermal conditions.

Embodiment 5

The method of any one of the previous embodiments, wherein the biomass feed comprises algae.

Embodiment 6

A method for hydrothermally processing biomass, comprising: contacting an algae-containing biomass feed having a phosphorus content with water under effective hydrothermal treatment conditions to produce a multi-phase product, the multi-phase product including a solids portion containing at least about 80% of the phosphorus content of the algae-containing biomass feed; separating the multi-phase product to produce at least a gas phase portion, a liquid hydrocarbon product, and the solids portion; and recycling phosphorus from the solids portion to an algae growth environment.

Embodiment 7

The method of embodiment 6, wherein recycling phosphorus from the solids portion comprises: extracting phosphorus from the solids portion to form a phosphorus based nutrient or nutrient precursor; and introducing the phosphorus based nutrient or nutrient precursor into the algae growth environment.

Embodiment 8

The method of embodiment 7, wherein the phosphorus based nutrient or nutrient precursor is phosphoric acid.

Embodiment 9

The method of any one of the previous embodiments, wherein the weight ratio of water to algae is from about 2:1 to about 10:1, for example from about 3:1 to about 5:1.

Embodiment 10

The method of any one of the previous embodiments, wherein the effective hydrothermal treatment conditions include a temperature from about 150° C. to about 500° C., for example from about 250° C. to about 375° C., and a pressure from about 25 barg (about 2.5 MPag) to about 300 barg (about 30 MPag).

Embodiment 11

The method of any one of the previous embodiments, wherein the effective hydrothermal treatment conditions include hydrothermal treatment in the presence of a catalyst, and wherein one of the following is satisfied: the processing time is from about 45 minutes to about 90 minutes when the temperature is from about 250° C. to about 300° C.; the processing time is from about 30 minutes to about 60 minutes when the temperature is from about 275° C. to about 325° C.; or the processing time is from about 15 minutes to about 30 minutes when the temperature is from about 300° C. to about 350° C.

Embodiment 12

The method of any one of the previous embodiments, wherein contacting the algae based feed with water under effective hydrothermal processing conditions substantially does not result in a phase change for the water.

Embodiment 13

The method of any one of the previous embodiments, further comprising separating the hydrocarbon liquid product to produce a fraction having at least 90% of its boiling range between about 193° C. to about 360° C.

Embodiment 14

The method of any one of the previous embodiments, wherein the phosphorus to carbon molar ratio of the solids portion is at least about 0.2, for example at least about 0.25, and wherein the solids portion optionally includes at least about 90% of the phosphorus content of the biomass feed.

Examples of Phosphorus Recovery

A series of experiments were performed to test phosphorus recovery from conventional solvent processing of an algae feed and from hydrothermal treatment of an algae feed. A commercially available freeze-dried Nannochloropsis algae sample was used for the experiments.

For the solvent processing, the solvent was a 50:50 mixture on a volume basis of $CHCl_3$ and $CH_3OH$. One part of the freeze-dried *Nannochloropsis* algae was combined with five pan s of the $CHCl_3/CH_3OH$ solvent and vigorously stirred for about 24 hours at room temperature (i.e., about 20-25° C.). Two distinct phases were apparent, a first phase containing the solvent and a solublized product, and a second phase containing solid remnants suspended and/or settled to the bottom of the solvent. The solids remnants were isolated and analyzed; the results of these characterizations are shown in Table 1 below.

For the hydrothermal treatment experiments, samples of the freeze-dried algae were mixed with water in a ratio of about four parts water to one part algae. The algae and water mixture was placed in 316SS stainless steel ~1-inch outer diameter reactors (Swagelok cap and plug). A nitrogen partial pressure of about 50 bar (about 5.0 MPa) was added to the reactor. A separate catalyst was not added to the reactor. The reactor was placed into a pre-heated ebullated sandbath. The reactors remained in the sandbath for about 60 minutes. Thereafter, the reactors were removed from the sandbath and quenched to approximately room temperature. The hydrocarbon products were recovered using methylene chloride extraction and phase separation. In the experiments described below, the temperature of the sandbath (and therefore the reactor) was about 200° C., about 300° C., or about 350° C.

Table 1 shows examples of processing of algae samples using solvent extraction and at the three hydrothermal processing temperatures. In the table, the term "phosphorus yield" refers to the weight percent of phosphorus from the initial sample that was contained in the solids product. Phosphorus concentration refers to the weight percent of phosphorus in the solids product. The P/C molar ratio refers to the molar ratio of phosphorus to carbon in the solids product. The phosphorus recovery efficiency is a measure of the relative amounts of phosphorus and carbon in the solids product. The phosphorus recovery efficiency is defined as $P_{recov\ eff} = P_{yield} \times [P_{moles}/(P_{moles}+C_{moles})]$.

In Table 1, Column A shows the results from analysis of the product solids from the solvent extraction. Columns B, C, and D show the results from analysis of the solids fraction from the hydrothermal treatments at about 200° C., about 300° C., and about 350° C., respectively.

TABLE 1

| | A (Solvent only) | B (200° C.) | C (300° C.) | D (350° C.) |
|---|---|---|---|---|
| P Yield (%) | 97 | 34 | 91 | 95 |
| P Conc. (wt %) | 1.55 | 2.16 | 30.8 | 21.8 |
| P/C molar ratio | 0.014 | 0.015 | 0.56 | 0.26 |
| P recovery effic. (%) | 1.3 | 0.5 | 32.5 | 19.8 |

As shown in Table 1, solvent extraction resulted in a relatively high phosphorus yield in the solids product of 97%. However, the solids product also included a large amount of other material, as shown by the overall weight percentage of phosphorus (1.55%). A large portion of this additional material was carbon, as shown by the phosphorus to carbon molar ratio (0.014). As a result, the phosphorus recovery efficiency, as defined above, was only 1.3%.

For the hydrothermal processing at about 200° C., the phosphorus yield was lower at about 34%. Because of the low initial recovery, and a relatively low concentration of phosphorus in the solids, the phosphorus recovery efficiency at about 200° C. was less than 1%.

At the higher processing temperatures, the phosphorus recovery efficiency was notably higher. At both ~300° C. and ~350° C., the phosphorus yield was greater than about 90%, indicating a good capture of the initial phosphorus in the solids product. Both the ~300° C. and ~350° C. experiments showed dramatically improved phosphorus recovery efficiencies, relative to the solvent extraction. This was due in part to the lower carbon content of the solids product, as the phosphorus to carbon molar ratio at both ~300° C. and ~350° C. was greater than about 0.25.

Additionally, the experiment at about 300° C. showed an unexpectedly improved result even relative to the experiment at about 350° C. Although the experiment at ~300° C. had a slightly lower phosphorus yield, the amount of carbon and other materials in the solids product was dramatically lower, as shown by the ~30.8 wt % phosphorus concentration and the phosphorus to carbon molar ratio of ~0.56. Without being bound by any particular theory, it is believed that the additional carbon present in the solids product at ~350° C. may be due to excess reaction with the feed. In an embodiment, the additional improved phosphorus recovery efficiency shown here at a ~300° C. processing temperature can be maintained for other feeds and at other reaction conditions by selecting reaction conditions that maintain a phosphorus yield of around 90%, such as a phosphorus yield from about 87% to about 93%.

The solids product generated by the experiment at ~300° C. was also analyzed using X-ray diffraction (XRD). Compounds that could be identified from the XRD spectrum included phosphates and phosphites. Some compounds identified in the scan were $Ca_{18}Mg_2H_2(PO_4)_{14}$; $Ca_{28.8}Fe_{3.2}(PO_4)_{21}O_{0.6}$; $Mg(PO_3)_2$; $Ca_2P_2O_7$; and $CaCO_3$.

Prophetic Example of Hydrothermal Processing

An algae feed is processed under hydrothermal treatment conditions in a continuous flow reaction system. The reaction zone for the hydrothermal treatment includes a coiled conduit surrounded by an oven. The coiling of the conduit increases the path length of the conduit within the oven. The flow rate within the conduit is selected so that feed has a residence time within the reaction zone of about 15 minutes. The temperature in the reaction zone is about 350° C. The feed passing through the reaction zone includes a mixture of algae and water with a water to algae weight ratio from about 10:1 to about 2.5:1. The pressure in the conduit is determined in part by the vapor pressure of water at the reaction temperature. If an optional catalyst is used (e.g., included with the feed), the pressure is also increased by the addition of about 2.5 MPa of hydrogen gas. After passing through the coiled conduit, the flow is passed into a separator. A gas phase product, a hydrocarbon product, an aqueous product, and a solids product are separated out. The solids product can have a phosphorus content that is at least 85% of the initial phosphorus content of the feed. The solids product can also have a phosphorus content that is at least about 20% of the total solids product.

What is claimed is:

1. A method for hydrothermally processing biomass, comprising:
   introducing a biomass feed having a water to biomass ratio of at least 1:1 into a reaction zone, the biomass feed having a phosphorus content;
   hydrothermally treating the biomass feed under effective hydrothermal treatment conditions to produce a multi-phase product, the multi-phase product including a solids portion containing at least about 80% of the phosphorus content of the biomass feed; and
   separating the multi-phase product to produce at least a gas phase portion, a liquid hydrocarbon product, and the solids portion.

2. The method of claim 1, wherein the biomass feed comprises algae, microalgae, or cyanobacteria.

3. The method of claim 2, wherein the weight ratio of water to algae is from about 2:1 to about 10:1.

4. The method of claim 1, wherein the effective hydrothermal treatment conditions include a temperature from about 150° C. to about 500° C. and a pressure from about 25 barg (about 2.5 MPag) to about 300 barg (about 30 MPag).

5. The method of claim 1, wherein the effective hydrothermal treatment conditions include a temperature from about 250° C. to about 375° C.

6. The method of claim 1, wherein the effective hydrothermal treatment conditions include hydrothermal treatment in the presence of a catalyst, and wherein one of the following is satisfied:
   the processing time is from about 45 minutes to about 90 minutes when the temperature is from about 250° C. to about 300° C.;
   the processing time is from about 30 minutes to about 60 minutes when the temperature is from about 275° C. to about 325° C.; or
   the processing time is from about 15 minutes to about 30 minutes when the temperature is from about 300° C. to about 350° C.

7. The method of claim 1, wherein contacting the algae based feed with water under effective hydrothermal processing conditions does not result in a phase change for the water.

8. The method of claim 1, further comprising separating the hydrocarbon liquid product to produce a fraction having at least 90 wt % of its boiling range between about 193° C. and about 360° C.

9. The method of claim 1, wherein the phosphorus to carbon molar ratio of the solids portion is at least about 0.2.

10. The method of claim 1, wherein the solids portion includes at least about 90% of the phosphorus content of the biomass feed and its phosphorus to carbon molar ratio is at least about 0.25.

11. The method of claim 9, wherein the biomass feed further comprises a multivalent metal.

12. The method of claim 11, wherein the multivalent metal comprises Ca, Mg, Fe, Al, or a combination thereof.

13. The method of claim 1, wherein the biomass feed further comprises a multivalent metal.

14. The method of claim 13, wherein the multivalent metal comprises Ca, Mg, Fe, Al, or a combination thereof.

15. A method for hydrothermally processing biomass, comprising:
   adding a multivalent metal to a biomass feed having a phosphorus content, the multivalent metal being added in a form suitable for increasing the amount of available multivalent metal cations in the biomass feed;
   contacting the biomass feed with water in the presence of the multivalent metal under effective hydrothermal treatment conditions to produce a multi-phase product, the multi-phase product including a solids portion containing at least about 80% of the phosphorus content of the biomass feed; and
   separating the multi-phase product to produce at least a gas phase portion, a liquid hydrocarbon product, and the solids portion.

16. The method of claim 15, wherein the multivalent metal comprises Ca, Mg, Fe, Al, or a combination thereof.

17. The method of claim 15, wherein contacting the biomass feed with water comprises contacting the biomass feed with water in the presence of about 0.1 wt % to about 1.0 wt % of the multivalent metal and in the presence of a catalyst, and wherein separating the multi-phase product to produce a solids portion comprises separating the multi-phase product to produce a catalyst portion and an algae-based solids portion.

18. The method of claim 17, wherein the algae-based solids portion includes at least about 80% of the phosphorus content of the biomass feed and includes a majority of the multivalent metal.

19. The method of claim 15, wherein the multivalent metal is added to the biomass feed in a reaction zone for the contacting of the biomass feed with water under effective hydrothermal conditions.

20. The method of claim 15, wherein the biomass feed comprises algae, microalgae, or cyanobacteria.

21. The method of claim 15, wherein the phosphorus to carbon molar ratio of the solids portion is at least about 0.2.

22. The method of claim 15, wherein the solids portion includes at least about 90% of the phosphorus content of the biomass feed and its phosphorus to carbon molar ratio is at least about 0.25.

23. A method for hydrothermally processing biomass, comprising:
   contacting an algae-containing feed having a phosphorus content with water under effective hydrothermal treatment conditions to produce a multi-phase product, the multi-phase product including a solids portion containing at least about 80% of the phosphorus content of the algae-containing feed;
   separating the multi-phase product to produce at least a gas phase portion, a liquid hydrocarbon product, and the solids portion; and
   recycling phosphorus from the solids portion to an algae growth process.

24. The method of claim 23, wherein recycling phosphorus from the solids portion comprises:
   extracting phosphorus from the solids portion to form a phosphorus based nutrient or nutrient precursor; and
   introducing the phosphorus based nutrient or nutrient precursor into the algae growth process.

25. The method of claim 23, wherein the phosphorus based nutrient or nutrient precursor is phosphoric acid.

26. The method of claim 23, wherein the weight ratio of water to algae is from about 3:1 to about 5:1.

27. The method of claim 23, wherein the solids portion includes at least about 90% of the phosphorus content of the biomass feed and its phosphorus to carbon molar ratio of at least about 0.25.

28. The method of claim 23, wherein the algae-containing feed further comprises a multivalent metal.

29. The method of claim 28, wherein the multivalent metal comprises Ca, Mg, Fe, Al, or a combination thereof.

* * * * *